United States Patent [19]
Conte et al.

[11] Patent Number: 5,780,057
[45] Date of Patent: Jul. 14, 1998

[54] PHARMACEUTICAL TABLET CHARACTERIZED BY A SHOWING HIGH VOLUME INCREASE WHEN COMING INTO CONTACT WITH BIOLOGICAL FLUIDS

[75] Inventors: Ubaldo Conte, Busto Arsizio; Lauretta Maggi, Pavia, both of Italy

[73] Assignee: Jagotec AG, Switzerland

[21] Appl. No.: 799,313

[22] Filed: Feb. 14, 1997

[30] Foreign Application Priority Data

Feb. 19, 1996 [IT] Italy .................. MI96A0311

[51] Int. Cl.⁶ .......................................... A61K 9/28
[52] U.S. Cl. .................. 424/468; 424/466; 424/472; 424/482
[58] Field of Search ................. 424/472, 466, 424/474, 475, 468, 482

[56] References Cited

U.S. PATENT DOCUMENTS

| 4,160,020 | 7/1979 | Ayer et al. | 424/15 |
| 4,839,171 | 6/1989 | Colombo et al. | 424/482 |
| 4,839,177 | 6/1989 | Columbo et al. | 424/482 |
| 5,487,901 | 1/1996 | Conte et al. | 424/472 |
| 5,650,169 | 7/1997 | Conte et al. | 424/472 |

*Primary Examiner*—Thurman K. Page
*Assistant Examiner*—Kathryne E. Shelborne

[57] ABSTRACT

A description is given of a pharmaceutical form for oral administration consisting of a two- or three-layers tablet, wherein at least one layer can rapidly swell by contact with biological and/or aqueous fluids, said swelling resulting in a considerable increase in the tablet volume. Said phenomenon determines a prolonged residence of the pharmaceutical form at the gastric level and therefore allows a slow release of the active ingredient from said pharmaceutical form to the stomach and/or the first tract of the intestine.

17 Claims, 2 Drawing Sheets

PHARMACEUTICAL TABLET CHARACTERIZED BY A SHOWING HIGH VOLUME INCREASE WHEN COMING INTO CONTACT WITH BIOLOGICAL FLUIDS

PRIOR ART

The development of ever more perfected active ingredient release systems, capable of liberating same according to release kinetics and procedures suitably designed to produce optimal medicinal effects has lately made considerable progress in pharmaceutical technology. Compared with conventional pharmaceutical forms, almost all controlled release systems (or depot forms) contain a much larger quantity of drug. It follows that the number of daily administrations may be drastically reduced and the posologic scheme simplified, i.e. instead of two, three or even more administrations/day, a single daily administration of a pharmaceutical form (or therapeutic system) containing a much larger dose of active ingredient can meet the daily drug requirements.

Preparations of this type have been used for a long time and may be easily found in commerce: among them, mention may be made of chronoids, microcapsules, tablets generally defined as "sustained release" type, enteric coated tablets and more complex preparations, such as erodible and/or swellable hydrophilic matrices.

More sophisticated therapeutic systems were recently developed, such as the so-called "reservoir" systems, the "push-pull" systems, osmotic pumps ("OROS") as disclosed in U.S. Pat. No. 4,160,020 (1979). Geomatrix systems as disclosed in U.S. Pat. No. 4,839,177 (1989) and No. 5,422,123 (1995). Said therapeutic systems have been thoroughly studied and amply used in the pharmaceutical field.

Now, most of said new systems can release the active ingredient contained therein at a constant rate (i.e. according to zero order kinetics), until complete release of same, independently of the pH of the gastrointestinal tract. It follows that said systems may find wide application only if the drugs may be uniformly absorbed in the gastrointestinal tract. However, serious troubles may arise when the active ingredients contained in said systems exhibit a small absorption window in said tract. In this case, only an extremely small amount of active ingredient may be absorbed and, therefore, produce the desired medicinal action, while most of the drug released cannot be absorbed since in some portions of the gastrointestinal tract, the substrate that is generally deputed to absorption, is unable to let the drug pass through the biological barriers.

In general, for a regular and prolonged drug absorption, a controlled release formulation must uniformly liberate the active ingredient in the various portions of the gastrointestinal tract, including the small intestine and the large intestine. The knowledge of the biopharmaceutical characteristics of the active ingredient and of the time of gastrointestinal transit of the pharmaceutical form is of major importance to provide formulations securing the desired medicinal effects in vivo.

In fact, the controlled release of active ingredients exhibiting a small absorption window in the first portion of the gastrointestinal tract, i.e. of substances that may be more effectively absorbed only in the stomach, duodenum and in the first portion of the small intestine, raises great difficulty since said active ingredients are to be released only in the portion capable of absorbing them.

SUMMARY

The pharmaceutical form of the present patent application is designed for a controlled release of the active ingredients that exhibit a small absorption window in the first portion of the gastrointestinal tract, i.e. of the substances that may be more effectively absorbed in the stomach, duodenum and in the first portion of the small intestine or of active ingredients that exert their action mostly at the gastric level.

The tablet claimed herein basically consists of two or three or more layers, i.e.

a) a layer 22 made by compression, which may optionally contain an active ingredient, generally consisting of erodible and/or gellable and/or swellable hydrophilic polymers. This layer besides acting as a barrier for drug release control is characterized in that it can rapidly swell, i.e. can markedly and rapidly increase in volume. Furthermore, said layer may have particular bioadhesive properties allowing the adhesion of the pharmaceutical form to the mucosa of the gastrointestinal tract or, by swelling, may also cause the floating of the pharmaceutical form on the gastric juice;

b) a layer 24 containing the active ingredient to be administered. This layer, applied by compression to layer 22, is made out of biodegradable and biocompatible polymeric materials, and other adjuvants whereby the formulation can be formed by compression and the active ingredient may be released within a time interval that may be predetermined by appropriate tests in vitro;

c) a third layer 26, if any, applied by compression to one of the aforementioned layers. Said third layer 26, which may optionally contain active ingredients, generally consists of erodible and/or gellable and/or swellable hydrophilic polymers, and acts as a barrier, i.e. is partially impermeable to the active ingredient contained in layer 24. As will be illustrated in detail in the examples reported hereinafter, layers 22 and 26 may have an identical composition and identical functional characteristics, i.e. may have the swelling properties described under a) and, at the same time, the drug release modulation properties described under c).

A characteristic of the present invention is that, owing to the rapid and considerable swelling of layer 22 and optionally also of layers 26 and 24, the pharmaceutical form, by contact with the gastric juice, increases in volume, which results in an increased residence time of same on the gastric level. It follows that the greater part of active ingredient contained therein may be released at a controlled rate in this portion of the gastrointestinal tract, where the absorption efficiency is the highest.

The claimed pharmaceutical form, designed for a controlled release of the active ingredients, is preferably cylindrical or lenticular in shape and consists of 2, 3 or more layers, of which at least one contains the active ingredient, while the other layer(s) does(do) not generally contain active ingredients, but consists(consist) of erodible and/or gellable and/or swellable hydrophilic polymers, either alone or in association with other adjuvants, whereby said pharmaceutical form can rapidly swell.

The formulation of said layers may also include polymeric substances allowing either the bioadhesion of the pharmaceutical form to the stomach or upper digestive tract, or the floating of the tablet in the gastric juice, which causes an increase in the tablet residence time in the stomach.

At least one of the two layers, 22 and 26, acts as a barrier, i.e. is partially impermeable, for a predeterminable time, to the active ingredient contained in layer 24, and at least one of the two layers, 22 and 26, is characterized in that it can rapidly swell, i.e. can rapidly increase in volume, and have particular bioadhesive properties allowing the pharmaceutical form positioning and adhesion to the mucosa of the first portion of the gastrointestinal tract. According to a further embodiment of the present invention, the three-layers tablet consists of layer 24, which contains a dose of active ingredient, of layer 22 as described above, and of layer 26, which contains a dose of active ingredient formulated for immediate release by contact with the gastric juice.

A benefit of the present invention is that said two- or three-layers pharmaceutical tablet is obtained by established compression procedures, well known to those skilled in the art.

DETAILED DESCRIPTION OF THE INVENTION

An object of the present invention is to provide a particular type of compressed tablet that, by contact with biological fluids, considerably increases in volume and exhibits a high residence time in the stomach and/or in the first portion of the gastrointestinal tract. The claimed tablet, intended for oral administration to humans and animals, consists of two or three or more layers, of which at least one contains an active ingredient exhibiting a small absorption window in the gastrointestinal tract or having to exert its action mostly at the gastric level.

A fundamental characteristic of the system is that at least one of the layers has such a composition that, when the pharmaceutical form comes into contact with the gastric juice, a considerable increase in the tablet volume takes place.

The structure of the new pharmaceutical form is schematically represented in FIGS. 1A - 4D and may be described as follows:

a) a first layer 22 generally consisting of erodible and/or gellable and at least partially swellable hydrophilic polymers, optionally in combination with other adjuvants. This layer, which is formed by compressing the ingredients in the powdered or granular form, can rapidly swell, i.e. rapidly increase in volume, and may have bioadhesive properties securing a prolonged adhesion to the mucosa of the first portion of the gastrointestinal tract. Otherwise, by swelling, this layer may optionally cause the floating of the pharmaceutical form on the gastric juice or defer the transfer of the pharmaceutical form to the duodenum through the pylorus until the increased volume of the layer is at least partially compensated by the partial dissolution and/or erosion of the tablet;

b) a second layer 24, adjacent to the first and containing the active ingredient, is made out of biodegradable and biocompatible polymeric materials and other adjuvants whereby the formulation can be formed by compression and the active ingredient may be released within a time interval that may be predetermined by preliminary tests in vitro;

c) an optional third layer 26 formed by compression and adjacent to the second layer 24. This layer generally consists of erodible and/or gellable and/or swellable hydrophilic polymers and, being initially impermeable to the active ingredient, acts as a barrier modulating the release of the active ingredient contained in adjacent layer 24.

Layer 26 may be identical with layer 22 in composition and functional characteristics, i.e. may considerably swell by contact with the gastric juice and therefore contribute to the volume increase of the pharmaceutical form.

Layer 26 too may contain the active ingredient, whose release differs from that of main layer 24, to which layer 26 is thus complementary. A characteristic of all possible embodiments of the invention is that the pharmaceutical form considerably increases in volume by contact with the gastric juice, due to the rapid and remarkable swelling of at least one of the aforesaid layers, 22 and 26, and to the optional swelling of layer 24.

This results in a much increased residence time of the tablet in the stomach and in the active ingredient absorption optimization. The claimed pharmaceutical form, designed for a controlled release of the active ingredients, is preferably cylindrical or lenticular in shape and consists of 2 or 3 or more layers, of which at least one contains the active ingredient, while the other layers do not generally contain the active ingredients, but consist of erodible and/or gellable and/or swellable hydrophilic polymers, either alone or in association with other adjuvants, whereby said pharmaceutical form can rapidly swell by at least 50% and preferably 100% of its initial volume. The formulation of said layers may also include polymeric substances allowing either the tablet bioadhesion to the stomach or its floating on the gastric juice, which results in an increased residence time in the stomach and, therefore, in an improved release of the active ingredient at the gastric level.

At least one of the two layers, 22 and 26, may act as a barrier, i.e. may initially be impermeable to the active ingredient contained in layer 24, and at least one of the two layers, 22 and 26, may rapidly swell, i.e. rapidly and considerably increase in volume, and may have bioadhesive properties securing a prolonged adhesion to the the mucosa of the first portion of the gastrointestinal tract.

A more rapid medicinal effect may be favoured by another pharmaceutical form of the invention, consisting of layer 24, which contains a dose of active ingredient to be released within a time interval that may be predetermined by preliminary tests in vitro, layer 22, as described above, which has the function rapidly to increase the volume of the pharmaceutical form, and a third layer, which contains a dose of active ingredient combined with suitable excipients for its immediate release by contact with the gastric juice.

The two- or three-layers tablet of the invention is obtained by well established compression procedures known to those skilled in the art. In any case, the pharmaceutical form described above, when coming into contact with the gastric juice and/or the fluids of the gastrointestinal tract, rapidly increases in volume and is structured as shown in FIGS. 1C, 1D, 2C, 2D, 3C, 3D, 4C, and 4D.

This increase in volume may involve one or more layer(s) of the tablet. The enlargement in size and the rate thereof may be followed and accurately evaluated by direct measurements or by a videomicroscope interfaced with a personal computer. The image is processed by an appropriate video image analysis dedicated programme. In fact, said technique makes it possible to study the in vitro behaviour of the formulations and, consequently, accurately to design pharmaceutical forms capable of meeting the morphological requirements, as well as to optimize the formulation of each layer to obtain a morphological behaviour answering the set target. By said technique, it is therefore possible accurately to predetermine which is the behaviour in vivo of the pharmaceutical form coming into contact with organic fluids. Furthermore, on the basis of appropriate tests in vitro, it is possible to schedule the release of the active ingredient contained in said pharmaceutical form within a prefixed time interval.

In fact, the determination of the morphological variations and of the active ingredient release profile (which may be obtained, e.g., by tests envisaged in pharmacopoeias) allows a very accurate prediction of the in vivo behaviour of the pharmaceutical form.

The polymeric substances used to prepare layers 22 and 26—which however may also be included in layer 24—are hydrophilic and slowly soluble and/or slowly gellable and/or erodible and/or at least partially swellable, either rapidly or at different rates, in aqueous fluids and are selected from the group consisting of hydroxymethylcellulose, hydroxyethylcellulose, hydroxypropyl methylcellulose having molecular weight from 1,000 to 4,000,000, hydroxypropyl cellulose having molecular weight from 2,000 to 2,000,000, carboxyvinyl polymers, polyvinyl alcohols, glucans, scleroglucans, chitosans, mannans, galactomannans, xantan gums, carrageenin and carrageenans, amylose, alginic acid and salts and derivatives thereof, acrylates, methacrylates, acrylic/methacrylic copolymers, polyanhydrides, polyamino acids, methyl vinyl ethers/maleic anhydride copolymers, carboxymethylcellulose and derivatives thereof, ethylcellulose, methylcellulose and cellulose derivatives in general.

The amount of said polymeric substances, in respect of the layer total weight, is of from 5% to 90% by wt. and preferably of from 20% to 85% by wt.

Layer 22 and sometimes, but not necessarily, layer 26 comprise hydrophilic polymeric substances facilitating the interaction between the components of the layer and the biological fluids with which said layer comes into contact, thus favouring a rapid and considerable volume increase of the pharmaceutical form.

These hydrophilic polymeric substances are selected from the group comprising the so-called "superdisgregating polymers", i.e. cross-linked polyvinylpyrrolidone, hydroxypropylcellulose and hydroxypropyl methylcellulose having molecular weight up to 150,000, cross-linked sodium carboxymethylcellulose, carboxymethyl starch, sodium carboxymethyl starch, potassium methacrylate-divinylbenzene copolymer, polyvinyl alcohols, amylose, cross-linked amylose, starch derivatives, microcrystalline cellulose and cellulose derivatives, alpha-, beta-and gamma-cyclodextrin and dextrin derivatives in general.

Said substances, in respect of the layer total weight, amount to 1% to 90% by wt. and preferably to 5% to 70% by wt.

Also substances from the group of surfactants (anionic, cationic and non-ionic) may be used. By facilitating wettability, said substances allow a more immediate interaction between the dissolution medium (or gastric juice) and the tablet, i.e. they cause a more rapid wettability and swelling of the pharmaceutical form and especially of the layer containing them. Among the substances having said characteristics, mention may be made of sodium lauryl sulphate, sodium ricinoleate, sodium tetradecyl sulphate, dioctyl sulphosuccinate, cetomacrogol, poloxamer, glyceryl monostearate, polysorbates, sorbitan monolaurate, lecithins and, in general, the pharmaceutically acceptable surfactants.

For the same purpose, the formulation of said layers may include absorbent hydrophilic substances, such as colloidal silica, starch, etc., which, due to their affinity for water or fluid, enhance the wettability and rapid swelling of the structure containing same.

It is also possible to use the so-called effervescent mixtures capable of producing a rapid interaction of the tablet or, in the specific case, of the layer with aqueous fluids and, preferably, with the gastric juice with which they come into contact.

Said substances fall into several groups, including the carbonates and bicarbonates of sodium and of other alkali or alkaline-earth metals, glycocoll sodium carbonate and other salts, either alone or in combination with pharmaceutically acceptable acids, such as citric, tartaric, adipic, ascorbic acids, capable of causing effervescence when said mixtures come into contact with aqueous fluids or an acid medium. By contact with the gastric juice and depending on the percent amount of the disgregating agent (or of another adjuvant) and on the percent amount of the gellable and/or erodible hydrophilic polymer present in the layer composition, said effervescence causes a rapid and considerable increase in the layer volume.

It is also possible to use other adjuvants selected from the group including classes of substances currently used in the pharmaceutical field, such as diluents, gliding substances, buffers, binding agents, adsorbers, etc., and in particular starch, pregelled starch, calcium phosphate, mannitol, lactose, xylitol, saccharose, glucose, sorbitol, microcrystalline cellulose; binding agents, such as gelatin, polyvinylpyrrolidone, methylcellulose, starch solution, ethylcellulose, arabic gum and tragacanth gum; lubricants, such as magnesium stearate, stearic acid, talc, colloidal silica, glyceryl monostearate, polyoxyethylene glycols having molecular weight from 400 to 60,000, hydrogenated castor oil, glyceryl behenate, waxes and mono-, bi-, and trisubstituted glycerides.

For example hydrophobic diluents such as glyceryl monostearate glyceryl behenate, hydrogenated castor oil, waxes and mono-, bi- and trisubstituted glycerides are used when water and/or aqueous fluids penetration into the medicated or barrier type layers has to be slowed down or alternatively the three layers tablets of the present invention may contain hydrophilic diluents favouring water penetrations such as mannitol, lactose, starch of various origin, sorbitol, xylitol, microcrystalline cellulose, colloidal silica.

The barrier type layer for example may contain adjuvants selected from the group consisting of glyceryl monostearate and derivative thereof, semisynthetic triglycerides, semisynthetic glycerides, hydrogenated castor oil, glycerylpalmitostearate, glyceryl behenate, cetyl alcohol, polyvinylpyrrolidone, glycerin, ethylcellulose, methylcellulose, sodium carboxymethylcellulose, magnesium stearate, stearic acid, talc, sodium benzoate, boric acid, polyoxyethylene glycols, colloidal silica and plasticizers used to provide said barrier type layers with the elasticity required and to improve the compressibility, adhesion and cohesion of the tablet such as hydrogenated castor oil, cetyl alcohol, cetylstearyl alcohol, fatty acids, glycerides and triglycerides as are or variously substituted, polyoxyethylene glycols and derivatives thereof having a molecular weight, ranging from 400 to 60,000.

The second layer 24 of the pharmaceutical tablet according to the present invention may contain hydrophilic and soluble and/or gellable and/or erodible and/or swellable polymers at a different rate such as hydroxymethylcellulose, hydroxyethylcellulose, hydroxypropyl methylcellulose having molecular weight of from 1,000 to 4,000,000, hydroxypropyl cellulose having molecular weight of from 2,000 to 2,000,000, carboxyvinyl polymers, chitosans, mannans, galactomannans, xanthan gums, carrageenin and carrageenans, amylose, alginic acid, salts and derivatives thereof, pectins, acrylates, methacrylates, acrylic/methacrylic copolymers, polyanhydrides, polyamino acids, methyl vinyl ethers/maleic anhydride copolymers, polyvinyl alcohols, glucans, scleroglucans, carboxymethylcellulose and derivatives thereof, ethylcellulose, methylcellulose and polyvinylpyrrolidone. These materials are contained in said second layer in amount generally comprised between 5 and 90% preferably between 20 and 85%.

Among the active ingredients that may be advantageously administered with the pharmaceutical form of the present invention mention may be made of all active ingredients exhibiting a small absorption window, preferably in the first portion of the gastrointestinal tract, such as for example: the calcium blockers: prazosin, ketanserin, guanabenz acetate, captopril, captopril hydrochloride, enalapril, enalapril maleate, lysinopril, hydralazide, methyldopa, methyldopa hydrochloride, levodopa, carbidopa, benserazide, amlodipine, nitrendipine, nifedipine, nicardipine, verapamil, or substances exerting an antiviral action, such as acyclovir, inosine, pranobex, tribavirine, vidarabine, zidovudine or AZT.

Furthermore, the pharmaceutical form of the invention may also contain active ingredients exerting a medicinal action at the gastric level, such as antiacids (aluminium hydroxide, magnesium carbonate, magnesium oxide), sucralphate, sodium carbenoxolone, pirenzepin, loperamide, cimetidine, ranitidine, famotidine, misoprostol, omeprazol.

The tablets of the invention can be prepared from powder and/or granular mixtures by conventional techniques; therefore, their production on an industrial scale is easily available. For example, they may be obtained by rotary presses suitable for producing multi-layer tablets, e.g. Layer-Press, Manesty, Liverpool, UK.

The thickness of the layers may range from 0.2 mm to 8 mm and preferably from 1 mm to 4 mm, depending on the quantity of active ingredient contained therein. The aforesaid presses usually operate at a pressure of from 1,000 to 5,000 kg/cm2 and produce, depending on the procedures adopted, which will be illustrated in detail in the examples conveyed hereinafter, cylindrical-, lenticular-, spheroid-, ovoid-shaped three-layer tablets suitable for easy administration and swallowing.

Furthermore, the pharmaceutical form may be coated with a polymeric film merely to provide protection or to slow down the active ingredient release starting phase. Said coating may be either soluble in an acid medium or permeable to allow the system activation (active ingredient release) only after a time interval that may be predetermined by in vitro tests.

EXAMPLE 1

Figure 3A:
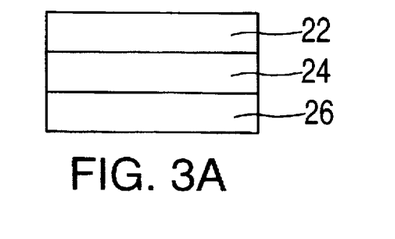
FIG. 3A represents a front view of a cylindrical tablet wherein layer 22 contains highly swellable polymers and layers 24 and 26 contain essentially erodible polymers.
Figure 3B:
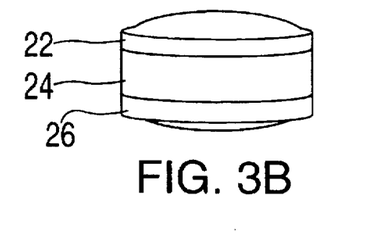
FIG. 3B represents a perspective view of a convex tablet wherein layers 22 contains highly swellable polymers and layers 24 and 26 contain essentially erodible polymers.
Figure 3C:
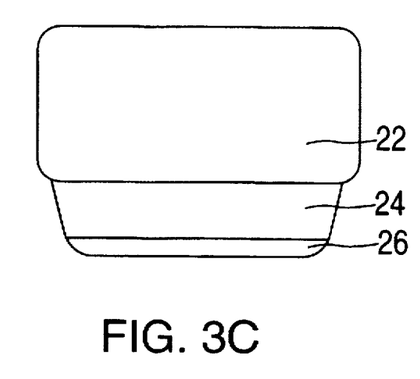
FIG. 3C represents a front view of a cylindrical tablet of FIG. 3A after swelling.
Figure 3D:
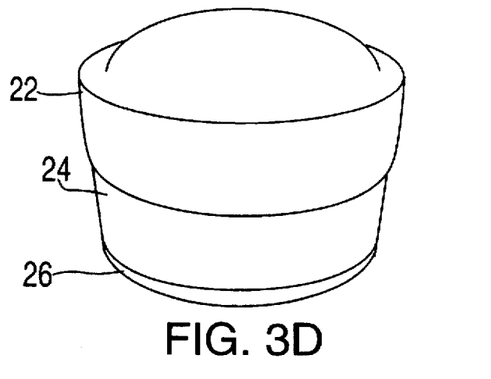
FIG. 3D represents a perspective view of a convex tablet of FIG. 3B after swelling.

Preparation of a set of 5,000 compressed tablets, as per FIG. 3A and FIG. 3B), containing zidovudine (or AZT) as an active ingredient (100 mg).

1.a—Preparation of the granular mass for the swellable layer (layer 22

The quantity of granular mass prepared was as necessary for the production of No. 5,000 swellable barrier-type layers (layer 22 of FIG. 3A and FIG. 3B) having the following percent composition:

| | |
|---|---|
| Scleroglucan (Actigum CS 11b, Sanofi, Paris, F) | 86.0 |
| Cross-linked sodium carboxymethylcellulose (AcDiSol, Type SD 711, FMC Corp., Philadelphia, USA) | 7.5 |
| Sodium laurylsulphate (USP grade, C.Erba, Milan, I) | 1.0 |
| Polyvinylpyrrolidone (Plasdone ® K29-32, ISP, Wayne, NY, USA) | 3.5 |
| Magnesium stearate (USP grade, C.Erba, Milan, I) | 1.0 |
| Colloidal silica (Syloid 244, Grace GmbH, Worms, D) | 1.0 |
| Total | 100.0 |

The granular mass was prepared by mixing scleroglucan, cross-linked sodium carboxymethylcellulose and sodium laurylsulphate in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 μm) to give uniformly sized granules. The granular mass was dried in an air oven at 40°–45° C. to constant weight, fed to a mixer for powders (Turbula, Mod. T2A), added with magnesium stearate and colloidal silica and mixed for 20'. The granular mass was compressed as described hereinafter.

1.b—Preparation of the granular mass containing the active ingredient

A granular mass for layer 24 of FIG. 3A and FIG. 3B) was prepared according to the procedure described hereinafter. Each layer contained 100 mg of active ingredient and had the following unitary composition:

| | |
|---|---|
| Zidovudine (or AZT) | 100.0 mg |
| Mannitol (USP grade, C.Erba, Milan, I) | 100.0 mg |

-continued

| | |
|---|---|
| Hydroxypropyl methylcellulose (Methocel ® K4M, Colorcon, Orpington, UK) | 50.0 mg |
| Polyvinylpyrrolidone (Plasdone ® K30, ISP, Wayne, NY, USA) | 15.0 mg |
| Magnesium stearate (USP grade, C.Erba, Milan, I) | 2.5 mg |
| Colloidal silica (Syloid 244, Grace GmbH, Worms, D) | 0.5 mg |
| Total | 268.0 mg |

The granular mass was prepared by mixing appropriate quantities of active ingredient, mannitol and hydroxypropyl methylcellulose in a sigma-type mixer, Mod. Erweka, type K5, (Frankfurt a. M., D.) The homogeneous powder mixture was wetted with a 10% w/v alcohol solution of polyvinylpyrrolidone and the uniformly wet mass was forced through a 25 mesh gauze (710 μm) to give uniformly sized granules. The granular mass was dried in an air oven at 40°–45° C. to constant weight, fed to a mixer for powders (Turbula, Mod. T2A, Bachofen, Basel, CH), added with magnesium stearate and colloidal silica and mixed for 20'. The granular mass was analyzed to determine the active ingredient content and compressed as described hereinafter.

1.c—Preparation of the granular mass for the barrier-type layer (layer 26

The quantity of granular mass as necessary for the production of No. 5,000 barrier-type layers (layer 26 of FIG. 3A and FIG. 3B) was prepared having the following percent composition:

| | |
|---|---|
| Hydroxypropyl methylcellulose (Methocel ® E5 Premium, Colorcon, Orpington, UK) | 26.7 |
| Lactose (USP grade, C.Erba, Milan, I) | 56.7 |
| Glyceryl behenate (Compritol 888 ATO-Gattefossé, FR) | 10.0 |
| Polyvinylpyrrolidone (Plasdone ® K29-32, ISP, Wayne, NY, USA) | 5.0 |
| Yellow lake (Eingemann Veronelli, Milan, I) | 0.1 |
| Magnesium stearate (USP grade, C.Erba, Milan, I) | 1.0 |
| Colloidal silica (Syloid 244, Grace GmbH, Worms, D) | 0.5 |
| Total | 100.0 |

The granular mass was prepared by mixing hydroxypropyl methylcellulose (Methocel® E 5, apparent viscosity 5 cps), lactose, glyceryl behenate and yellow lake in a sigma-type mixer, Mod. Erweka, type K5, Frankfurt a. M., D. The homogeneous powder mixture was wetted with a 10% w/v solution of polyvinylpyrrolidone in a 1:1 water/ethanol mixture and the uniformly wet mass was forced through a 25 mesh gauze (710 μm) to give pale yellow uniformly sized granules. The granular mass was dried in an air oven at 40°–45° C. to constant weight, fed to a mixer for powders (Turbula, Mod. T2A), added with magnesium stearate and colloidal silica and mixed for 20'. The granular mass was compressed as described hereinafter.

1.d—Preparation of three-layer tablets (by compression)

The granular masses obtained as reported in the previous sections and according to schemes well known to those skilled in the art were loaded into three feed hoppers of a rotary press fit for producing three-layers tablets (e.g. Layer-press, Manesty, Liverpool, UK). In particular, the first hopper was fed with the granular mass as per point 1.a, the second hopper was fed with the granular mass as per point 1.b and the third hopper was fed with the granular mass as per point 1.c.

The press was equipped with circular flat punches, 10 mm in diameter and set to produce three-layer tablets, i.e. a first 150 mg barrier-type layer (this being the quantity necessary to obtain a thickness of approx. 1.3 mm), a second layer consisting of 268 mg of granular mass containing the active ingredient (equalling 100 mg ATZ), and a third 100 mg barrier-type layer (this being the quantity necessary to obtain a thickness of approx. 1.0 mm). The three-layers tablets obtained by operating as described above, at a pressure of 2,000 kg/cm2, averagely weighed 518 mg and contained 100 mg of active ingredient.

1.e—Dissolution test

The tablet release characteristics were evaluated by apparatus 2 (paddle) disclosed in USP XXIII, operating at 100 rpm. The dissolution fluid was deionized water at 37° C. Drug release was controlled by UV spectrophotometer set at 266 nm, using an automatic sampling and reading system (Spectracomp 602, Advanced Products, Milan, Italy). The results obtained are shown in Table 1.

TABLE 1

| Time (hrs) | Release (%) |
|---|---|
| 1 | 13.6 |
| 2 | 27.2 |
| 3 | 40.3 |
| 4 | 52.0 |
| 5 | 62.2 |
| 6 | 72.1 |
| 7 | 81.5 |
| 8 | 90.8 |
| 9 | 98.6 |
| 10 | 100.1 |

The above data provide evidence of a controlled drug release from the systems so prepared over a period of approx. 9–10 hrs.

1.f—Swelling test

The test was conducted under the same experimental conditions as adopted for the dissolution test. At adequate time intervals, the tablets were collected from the dissolution medium. The tablets volume and the sizes of the different layers were measured by a videomicroscope (VS-90, interfaced with a video image analysis dedicated system, CV 9000, FKV, Sorisole, Bergamo, I). The results obtained are shown in Table 2.

TABLE 2

| Time (hrs) | Nucleus + barrier volume (layers 1.b + 1.c) %* | Swellable layer volume (layer 1.a) %* |
|---|---|---|
| 0 | 100.0 | 100.0 |
| 0.5 |  | 213.8 |
| 1 | 124.9 | 241.4 |
| 1.5 | 139.5 | 253.5 |
| 2 | 178.5 | 287.8 |
| 2.5 | 184.7 | 322.3 |
| 3 | 190.9 | 346.8 |
| 4 | 209.6 | 363.1 |
| 5 | 232.8 | 408.2 |
| 6 | 257.0 | 436.9 |
| 7 | 255.2 | 461.5 |
| 8 | 259.1 | 478.9 |

*% volume of the initial volume

As may be seen, in the systems prepared, the size of the swellable layer increases considerably, i.e. up to 5 times its initial volume. This phenomenon is particularly evident from a comparison with the volume increase of the other two layers: the nucleus and barrier total swelling comes to two times and a half the initial volume. Furthermore, compared with the other two layers, the swellable layer increases in volume at a much higher rate. Said behaviour fully matches the goals of the present invention.

EXAMPLE 2

Figure 1A:
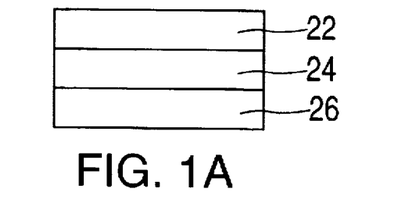
FIG. 1A represents a front view of a cylindrical three layer tablet wherein layers 22 and 26 contain highly swellable polymers.
Figure 1B:
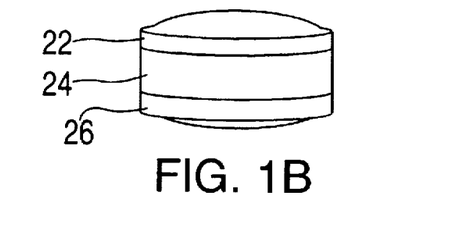
FIG. 1B represents a perspective view of a convex three layer tablet wherein layers 22 and 26 contain highly swellable polymers.
Figure 1C:
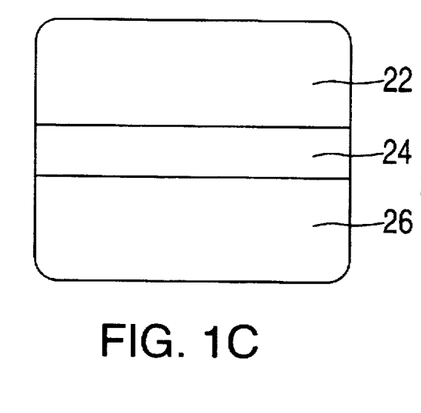
FIG. 1C represents a front view of a cylindrical three layer tablet of FIG. 1A after swelling.
Figure 1D:
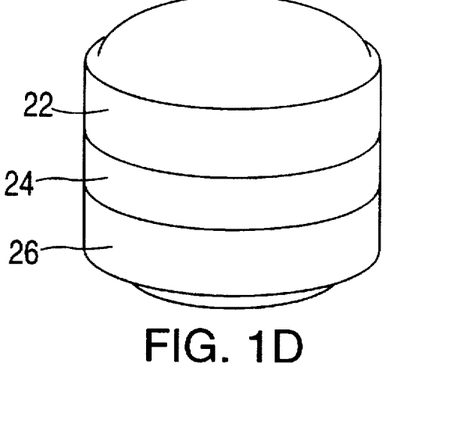
FIG. 1D represents a perspective view of a convex three layer tablet of FIG. 1B after swelling.
Figure 2A:
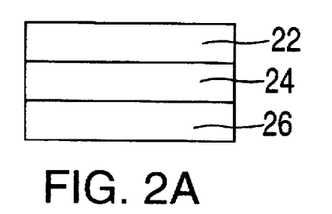
FIG. 2A represents a front view of a cylindrical three layer tablet wherein layer 22 contains highly swellable polymers and layer 24 contains swellable polymers.
Figure 2B:
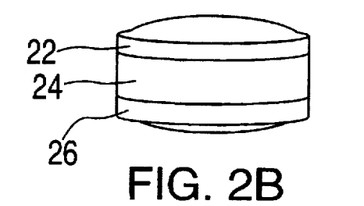
FIG. 2B represents a perspective view of a convex three layer tablet wherein layer 22 contains highly swellable polymers and layer 24 contains swellable polymers.
Figure 2C:
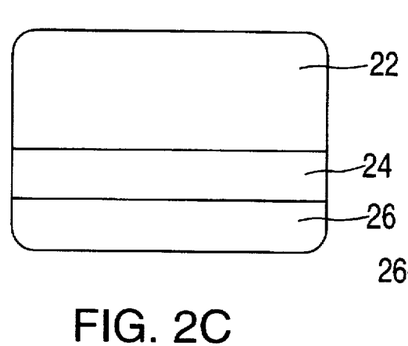
FIG. 2C represents a front view of a cylindrical three layer tablet of FIG. 2A after swelling.
Figure 2D:
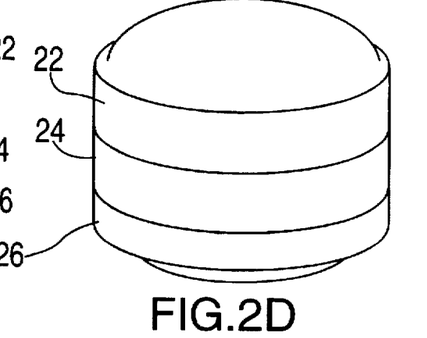
FIG. 2D represents a perspective view of a convex three layer tablet of FIG. 2B after swelling.

Preparation of a set of 5,000 compressed tablets, as per FIG. 2A and FIG. 2B), containing acyclovir as an active ingredient (100 mg).

2.a—Preparation of the granular mass for the swellable layer (layer 22

The quantity of granular mass prepared for the production of No. 5,000 swellable barrier-type layers (layer 22 of FIG. 2A and FIG. 2B) was prepared, having the following percent composition:

| | |
|---|---|
| Hydroxypropyl methylcellulose (Methocel ® K15M, Colorcon, Orpington, UK) | 50.0 |
| Cross-linked sodium carboxymethylcellulose (AcDiSol, Type SD 711, FMC Corp., Philadelphia, USA) | 45.0 |
| Polyvinylpyrrolidone (Plasdone ® K29-32, ISP, Wayne, NY, USA) | 3.4 |
| Red lake (Eingemann Veronelli, Milan, I) | 0.1 |
| Magnesium stearate (USP grade, C.Erba, Milan, I) | 1.0 |
| Colloidal silica (Syloid 244, Grace GmbH, Worms, D) | 0.5 |
| Total | 100.0 |

The granular mass was prepared by mixing hydroxypropyl methylcellulose (Methocel® K15M, apparent viscosity 15,000 cps), red lake and cross-linked sodium carboxymethylcellulose in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 µm) to give uniformly sized pink granules. The granular mass was dried in an air oven at 40°–45° C. to constant weight, fed to a mixer for powders (Turbula, Mod. T2A), added with magnesium stearate and colloidal silica and mixed for 20'. The granular mass was compressed as described hereinafter.

2.b—Preparation of the granular mass containing the active ingredient

A granular mass was prepared according to the procedure described hereinafter and used for the preparation of layer 24 of FIG. 2A and FIG. 2B), having the following composition:

| | |
|---|---|
| Acyclovir (USP grade) | 100.0 mg |
| Lactose (USP grade, C.Erba, Milan, I) | 106.8 mg |
| Microcrystalline cellulose (Avicel Ph 102, FMC Corp., Philadelphia, PA, USA) | 26.2 mg |
| Hydroxypropyl methylcellulose (Methocel ® K4M, Colorcon, Orpington, UK) | 10.0 mg |
| Polyvinylpyrrolidone (Plasdone ® K30, ISP, Wayne, NY, USA) | 5.0 mg |
| Carboxymethyl starch (Explotab, Mendel, Carmel, NY, USA) | 10.0 mg |
| Magnesium stearate (USP grade, C.Erba, Milan, I) | 2.0 mg |
| Colloidal silica (Syloid 244, Grace GmbH, Worms, D) | 1.0 mg |
| Total | 261.0 mg |

The granular mass was prepared by mixing appropriate quantities of active ingredient, lactose, microcrystalline cellulose and hydroxypropyl methylcellulose (Methocel® K4M, apparent viscosity 4,000 cps) in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 µm) to give uniformly sized granules. The granular mass was dried in an air oven at 40°–45° C. to constant weight, fed to a mixer for powders (Turbula, Mod. T2A, Bachofen, Basel, CH), added with carboxymethyl starch, magnesium stearate and colloidal silica and mixed for 20'. The granular mass was compressed as described hereinafter.

2.c—Preparation of the granular mass for the barrier-type layer (layer 26

The granular mass was prepared as described in Example 1, point 1.c.

2.d—Preparation of three-layer tablets (by compression)

The granular masses obtained as reported in the previous sections and according to schemes well known to those skilled in the art were loaded into three feed hoppers of a rotary press fit for producing three-layer tablets (e.g. Layerpress, Manesty, Liverpool, UK). In particular, the first hopper was fed with the granular mass as per point 2.a, the second hopper was fed with the granular mass as per point 2.b and the third hopper was fed with the granular mass as per point 2.c.

The press was equipped with circular concave punches, 11 mm in diameter, and set to produce three-layer tablets, i.e. a first 170 mg swellable layer 22 (this being the quantity necessary to obtain a thickness of approx. 1.3 mm), a second layer 24 consisting of 261 mg of granular mass containing the active ingredient (equalling 100 mg acyclovir), and a third 120 mg barrier-type layer 24 (this being the quantity necessary to obtain a thickness of approx. 1.0 mm). The three-layer tablets obtained by operating as described above averagely weighed 551 mg and contained 100 mg of active ingredient.

2.e—Dissolution test

The tablet release characteristics were evaluated by apparatus 2 (paddle) disclosed in USP XXII, operating at 100 rpm. The dissolution fluid was simulated gastric juice at pH 1.2 (as per USP) at 37° C. Drug release was controlled by UV spectrophotometer set at 221 nm, using an automatic sampling and reading system (Spectracomp 602, Advanced Products, Milan, Italy).

The results obtained are shown in Table 3.

TABLE 3

| Time (min) | Release (%) |
|---|---|
| 15 | 22.6 |
| 30 | 36.6 |
| 60 | 55.6 |
| 90 | 71.1 |
| 120 | 84.4 |
| 150 | 94.9 |
| 180 | 100.3 |

The above data provide evidence of a controlled drug release from the systems so prepared over a period of approx. 3 hrs.

2.f—Swelling test

The test was conducted under the same experimental conditions as adopted for the dissolution test. Volume variations were determined as per Example 1, point 1.f. The results obtained are shown in Table 4.

TABLE 4

| Time (min) | Nucleus + barrier volume (layers 2.b + 2.c) %* | Swellable layer volume (layer 2a) %* |
|---|---|---|
| 0 | 100.0 | 100.0 |
| 30 | 168.9 | 381.0 |
| 60 | 210.1 | 443.7 |
| 90 | 267.1 | 462.5 |
| 120 | 249.2 | 504.1 |
| 150 | 206.0 | 528.0 |

TABLE 4-continued

| Time (min) | Nucleus + barrier volume (layers 2.b + 2.c) %* | Swellable layer volume (layer 2a) %* |
|---|---|---|
| 180 | 193.5 | 552.2 |
| 210 | 125.0 | 594.3 |

*% volume of the initial volume

As may be seen, in the systems prepared, the size of the swellable layer increases considerably, i.e. up to 6 times its initial volume. This phenomenon is particularly evident from a comparison with the volume increase of the other two layers: the nucleus and barrier total swelling comes to two times and a half initial volume, but then tend to dissolve in the dissolution medium. Furthermore, compared with the other two layers, the swellable layer increases in volume at a much higher rate. Said behaviour fully matches the goals of the present invention.

EXAMPLE 3

Preparation of a set of 5.000 compressed tablets, as per FIG. 2A and FIG. 2B), containing acyclovir as the active ingredient (50 mg).

3.a—Preparation of the granular mass for the swellable layer (layer 22

A granular mass was prepared necessary for the production of No. 5.000 swellable barrier-type layers (layer 22 of FIG. 2A and FIG. 2B), having the following percent composition:

| | |
|---|---|
| Galactomannan (Viscogum HV 3000a, Sanofi, Paris, F) | 45.0 |
| Cross-linked sodium carboxymethylcellulose (AcDiSol, Type SD 711, FMC Corp., Philadelphia, USA) | 5.0 |
| Lactose (USP grade, C.Erba, Milan, I) | 35.0 |
| Glyceryl behenate (Compritol 888 ATO, Gattefossé, FR) | 10.0 |
| Polyvinylpyrrolidone (Plasdone ® K29-32, ISP, Wayne, NY, USA) | 3.5 |
| Magnesium stearate (USP grade, C.Erba, Milan, I) | 1.0 |
| Colloidal silica (Syloid 244, Grace GmbH, Worms, D) | 0.5 |
| Total | 100.0 |

The granular mass was prepared by mixing galactomannan, lactose, glyceryl behenate and cross-linked sodium carboxymethylcellulose in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 µm) to give uniformly sized granules. The granular mass was dried in an air oven at 40°–45° C. to constant weight, fed to a mixer for powders (Turbula, Mod. T2A), added with magnesium stearate and colloidal silica and mixed for 20'. The granular mass was compressed as described hereinafter.

3.b—Preparation of the granular mass containing the active ingredient

A granular mass was prepared and used for the preparation of layer 24 of FIG. 2A and FIG. 2B), containing 50 mg active ingredient and having the following composition:

| | |
|---|---|
| Acyclovir (USP grade) | 50.0 mg |
| Lactose (USP grade, C.Erba, Milan, I) | 53.4 mg |
| Microcrystalline cellulose (Avicel Ph 102, FMC Corp., Philadelphia, PA, USA) | 13.1 mg |
| Hydroxypropyl methylcellulose (Methocel ® K4M, Colorcon, Orpington, UK) | 5.0 mg |
| Polyvinylpyrrolidone (Plasdone ® K30, ISP, Wayne, NY, USA) | 2.5 mg |
| Carboxymethyl starch (Explotab, Mendel, Carmel, NY, USA) | 5.0 mg |
| Magnesium stearate (USP grade, C.Erba, Milan, I) | 1.0 mg |
| Colloidal silica (Syloid 244, Grace GmbH, Worms, D) | 0.5 mg |
| Total | 130.5 mg |

The granular mass was prepared by mixing the active ingredient, lactose, microcrystalline cellulose and hydroxypropyl methylcellulose (Methocel® K4M, apparent viscosity 4.000 cps) in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 µm) to give uniformly sized granules. The granular mass was dried in an air oven at 40°–45° C. to constant weight, fed to a mixer for powders (Turbula, Mod. T2A, Bachofen, Basel, CH), added with carboxymethyl starch, magnesium stearate and colloidal silica and mixed for 20'. The granular mass was compressed as described hereinafter.

3.c—Preparation of the granular mass for the barrier-type layer (layer 26

A granular mass was prepared for the production of No. 5.000 barrier-type layers (layer 26 of FIG. 2A and FIG. 2B), having the following percent composition:

| | |
|---|---|
| Hydroxypropyl methylcellulose (Methocel ® E15 LV, Colorcon, Orpington, UK) | 36.7 |
| Lactose (USP grade, C.Erba, Milan, I) | 56.7 |
| Polyvinylpyrrolidone (Plasdone ® K29-32, ISP, Wayne, NY, USA) | 5.0 |
| Green lake (Eingemann Veronelli, Milan, I) | 0.1 |
| Magnesium stearate (USP grade, C.Erba, Milan, I) | 1.0 |
| Colloidal silica (Syloid 244, Grace GmbH, Worms, D) | 0.5 |
| Total | 100.0 |

The granular mass was prepared by mixing appropriate quantities of hydroxypropyl methylcellulose (Methocel® E15LV, apparent viscosity 15 cps), lactose and green lake in a sigma-type mixer, Mod. Erweka, type K5, Frankfurt a. M., D. The homogeneous powder mixture was wetted with a 10% w/v solution of polyvinylpyrrolidone in a 1:1 water/ethanol mixture and the uniformly wet mass was forced through a 25 mesh gauze (710 µm) to give pale green uniformly sized granules. The granular mass was dried in an air oven at 40°–45° C. to constant weight, fed to a mixer for powders (Turbula, Mod. T2A), added with magnesium stearate and colloidal silica and mixed for 20'. The granular mass was compressed as described hereinafter.

3.d—Preparation of three-layers tablets (by compression)

The granular masses obtained as reported in the previous sections and according to schemes well known to those skilled in the art were loaded into three feed hoppers of a rotary press fit for producing three-layer tablets (e.g. Layerpress, Manesty, Liverpool, UK). In particular, the first hopper was fed with the granular mass as per point 3.a, the second hopper was fed with the granular mass as per point 3.b and the third hopper was fed with the granular mass as per point 3.c.

The press was equipped with circular concave punches, 7 mm in diameter, and set to produce three-layer tablets, i.e. a first 70 mg barrier-type layer 22 (this being the quantity necessary to obtain a thickness of approx. 1.3 mm), a second

15 layer 24 consisting of 130.5 mg of granular mass containing the active ingredient (equalling 50 mg acyclovir), and a third 40 mg barrier-type layer (this being the quantity necessary to obtain a thickness of approx. 1.0 mm). The three-layer tablets obtained by operating as described above averagely weighed 240.5 mg and contained 50 mg of active ingredient.

3.e—Dissolution test

The test was conducted as per Example 2, point 2.e. The results obtained are shown in Table 5.

TABLE 5

| Time (min) | Release (%) |
|---|---|
| 15 | 19.9 |
| 30 | 32.2 |
| 60 | 51.5 |
| 90 | 66.2 |
| 120 | 77.8 |
| 150 | 85.5 |
| 180 | 92.9 |
| 210 | 96.6 |
| 240 | 98.5 |
| 270 | 100.0 |

The above data provide evidence of a controlled drug release from the systems so prepared over a period of approx. 4 hrs.

3.f—Swelling test

The test was conducted as per Example 2, point 2.f. The results obtained are shown in Table 6.

TABLE 6

| Time (min) | Nucleus – barrier volume (layers 3.b + 3.c) %* | Swellable layer volume (layer 3a) %* |
|---|---|---|
| 0 | 100.0 | 100.0 |
| 30 | 155.9 | 228.6 |
| 60 | 203.8 | 250.4 |
| 90 | 221.6 | 270.7 |
| 120 | 228.1 | 298.4 |
| 150 | 223.8 | 322.2 |
| 180 | 179.7 | 335.5 |
| 210 | 120.0 | 375.3 |

*% volume of the initial volume

As may be seen, in the systems prepared, the size of the swellable layer increases considerably, i.e. up to almost 4 times its initial volume. This phenomenon is particularly evident from a comparison with the volume increase of the other two layers: the nucleus and barrier total swelling comes to approx. two times, but then tend to dissolve in the dissolution medium. Furthermore, compared with the other two layers, the swellable layer increases in volume at a much higher rate. Said behaviour fully matches the goals of the present invention.

EXAMPLE 4

Figure 4A:
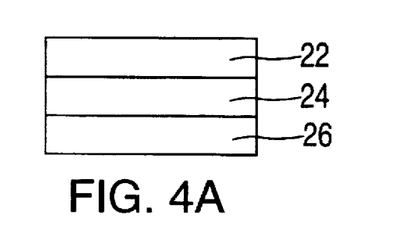
FIG. 4A represents a front view of a cylindrical tablet wherein layer 22 contains highly swellable polymers; layer 24 contains erodible and swellable polymers and layer 26 contains the active principle and hydrophilic diluents.
Figure 4B:
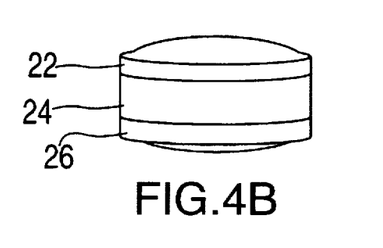
FIG. 4B represents a perspective view of a convex tablet wherein layer 22 contains highly swellable polymers; layer 24 contains erodible and swellable polymers and layer 26 contains the active principle and hydrophilic diluents.
Figure 4C:
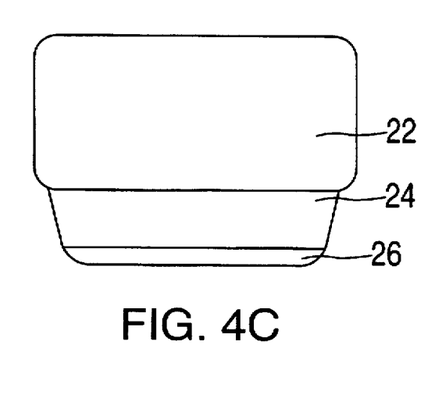
FIG. 4C represents a front view of a cylindrical tablet of FIG. 4A after swelling.
Figure 4D:
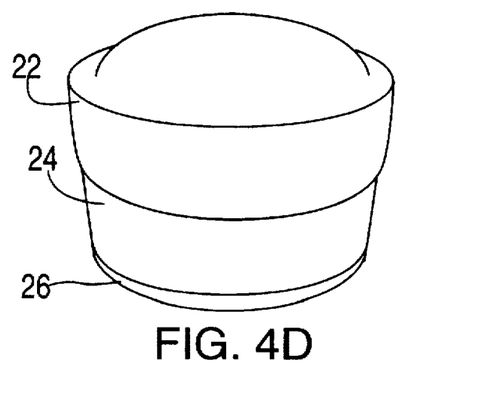
FIG. 4D represents a perspective view of a convex tablet of FIG. 4B after swelling.

Preparation of a set of 5,000 tablets, as per FIG. 4A and FIG. 4B), containing ranitidine as an active ingredient (two doses of 100 mg each).

4.a—Preparation of the granular mass for the swellable layer

The granular mass was prepared for the production of No. 5,000 swellable barrier-type layers (layer 22 of FIG. 4A and FIG. 4B) having the following percent composition:

| | |
|---|---|
| Hydroxypropyl methylcellulose (Methocel ® K4M, Colorcon, Orpington, UK) | 50.0 |
| Lactose (USP grade, C.Erba, Milan, I) | 35.0 |

16

-continued

| | |
|---|---|
| Carboxyvinyl polymer (Carbopol 934 PH, Goodrich, USA) | 5.0 |
| Cross-linked polyvinylpyrrolidone (Polyplasdone ® ISP, Wayne, NY, USA) | 5.0 |
| Blue lake (Eingemann Veronelli, Milan, I) | 0.1 |
| Polyvinylpyrrolidone (Plasdone ® K29-32, ISP, Wayne, NY, USA) | 3.4 |
| Magnesium stearate (USP grade, C.Erba, Milan, I) | 1.0 |
| Colloidal silica (Syloid 244, Grace GmbH, Worms, D) | 0.5 |
| Total | 100.0 |

The granular mass was prepared by mixing the appropriate quantities of hydroxypropyl methylcellulose (Methocel® K4M, apparent viscosity 4,000 cps), blue lake and lactose in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 μm) to give uniformly sized blue granules. The granular mass was dried in an air oven at 40°–45° C. to constant weight, fed to a mixer for powders (Turbula, Mod. T2A), added with magnesium stearate and colloidal silica and mixed for 20'. The granular mass was compressed as described hereinafter.

4.b—Preparation of the controlled release granular mass containing the second dose of active ingredient (100 mg)

A granular mass was prepared and used for the preparation of layer 24 of FIG. 4A and FIG. 4B), containing 100 mg active ingredient and having the following composition:

| | |
|---|---|
| Ranitidine hydrochloride (equalling 100 mg as a basis) | 112.0 mg |
| Hydroxypropyl methylcellulose (Methocel ® K15M, Colorcon, Orpington, UK) | 20.0 mg |
| Mannitol (USP grade, C.Erba, Milan, I) | 20.0 mg |
| Polyvinylpyrrolidone (Plasdone ® K30, ISP, Wayne, NY, USA) | 8.3 mg |
| Talc (USP grade, C. Erba, Milan, I) | 2.7 mg |
| Magnesium stearate (USP grade, C.Erba, Milan, I) | 1.0 mg |
| Total | 164.0 mg |

The granular mass was prepared by mixing appropriate quantities of hydroxypropyl methylcellulose (Methocel® K15M, apparent viscosity 15,000 cps) and mannitol in a sigma-type mixer, Mod. Erweka, type K5, Frankfurt a. M., D. The homogeneous powder mixture was wetted with a 10% w/v solution of polyvinylpyrrolidone in 1:1 water/ ethanol mixture and the uniformly wet mass was forced through a 25 mesh gauze (710 μm) to give uniformly sized granules. The granular mass was dried in an air oven at 40°–45° C. to constant weight, fed to a mixer for powders (Turbula, Mod. T2A, Bachofen, Basel, CH), added with talc and magnesium stearate and mixed for 20'. The granular mass was compressed as described hereinafter.

4.c—Preparation of the granular mass containing a fast release dose of active ingredient (100 mg)

A granular mass was prepared and used for the preparation of layer 26 of FIG. 4A and FIG. 4B), containing 100 mg active ingredient and having the following composition:

| | |
|---|---|
| Ranitidine hydrochloride (corresponding to 100 Ranitidine) | 112.0 mg |
| Microcrystalline cellulose (Avicel Ph 102, FMC Corp., Philadelphia, PA, USA) | 80.0 mg |
| Polyvinylpyrrolidone (Plasdone ® K30, ISP, Wayne, NY, USA) | 5.2 mg |
| Cross-linked polyvinylpyrrolidone (Polyplasdone | 3.0 mg |

-continued

| | |
|---|---|
| XL ® ISP, Wayne, NY, USA) | |
| Magnesium stearate (USP grade, C.Erba, Milan, I) | 1.0 mg |
| Colloidal silica (Syloid 244, Grace GmbH, Worms, D) | 0.3 mg |
| Total | 201.5 mg |

The granular mass was prepared by mixing appropriate quantities of active ingredient and microcrystalline cellulose in a sigma-type mixer, Mod. Erweka, type K5, Frankfurt a. M., D. The homogeneous powder mixture was wetted with a 10% w/v alcohol solution of polyvinylpyrrolidone and the uniformly wet mass was forced through a 25 mesh gauze (710 μm) to give uniformly sized granules. The granular mass was dried in an air oven at 40°–45° C. to constant weight, fed to a mixer for powders (Turbula, Mod. T2A, Bachofen, Basel, CH), added with cross-linked polyvinylpyrrolidone, magnesium stearate and colloidal silica, and mixed for 20'. The granular mass was compressed as described hereinafter.

4.d—Preparation of three-layer tablets (by compression)

The granular masses obtained as reported in the previous sections and according to schemes well known to those skilled in the art were loaded into three feed hoppers of a rotary press fit for producing three-layer tablets (e.g. Layer-press, Manesty, Liverpool, UK). In particular, the first hopper was fed with the granular mass as per point 4.a, the second hopper was fed with the granular mass as per point 4.b and the third hopper was fed with the granular mass as per point 4.c.

The press was equipped with circular concave punches, 8 mm in diameter, and set to produce three-layer tablets, i.e. a first 50 mg swellable barrier-type layer 22 (this being the quantity necessary to obtain a thickness of approx. 1.0 mm), a second layer 24 consisting of 164 mg of delayed release granular mass containing 100 mg ranitidine and a third 201.5 mg fast release granular mass (layer 26 containing 100 mg ranitidine. The three-layer tablets obtained by operating as described above averagely weighed 415.5 mg and contained 200 mg of active ingredient.

4.e—Dissolution test

The tablet release characteristics were evaluated by apparatus 2 (paddle) disclosed in USP XXII, operated at 100 rpm. The dissolution fluid was deionized water at 37° C. Drug release was controlled by UV spectrophotometer set at 313 nm, using an automatic sampling and reading system (Spectracomp 602, Advanced Products, Milan, Italy). The results obtained are shown in Table 7.

TABLE 7

| Time (min) | Release (%) |
|---|---|
| 15 | 48.1 |
| 30 | 52.8 |
| 60 | 61.3 |
| 90 | 70.6 |
| 120 | 78.1 |
| 150 | 84.1 |
| 180 | 90.0 |
| 210 | 93.9 |
| 240 | 96.1 |
| 300 | 100.3 |

The above data provide evidence of a controlled drug release from the systems so prepared over a period of approx. 4–5 hrs.

4.f—Swelling test

The test was conducted as per Example 1, point 1.f., under the same experimental conditions as adopted for the dissolution test. The results obtained are shown in Table 8.

TABLE 8

| Time (min) | Fast release layer + delayed release layer volume (4b + 4c) %* | Swellable layer volume (layer 4a) %* |
|---|---|---|
| 0 | 100.0 | 100.0 |
| 30 | 121.0 | 186.1 |
| 60 | 129.2 | 241.0 |
| 90 | 149.4 | 267.2 |
| 120 | 146.3 | 305.0 |
| 150 | 142.0 | 356.1 |
| 180 | 122.0 | 398.0 |
| 240 | 106.0 | 429.3 |

*% volume of the initial volume

As may be seen, in the systems prepared, the size of the swellable layer increases considerably, i.e. up to over 4 times its initial volume. This phenomenon is particularly evident from a comparison with the increase in volume of the other two layers, which do not tend to swell, but rather tend to dissolve in the dissolution medium. Said behaviour fully matches the goals of the present invention.

We claim:

1. A pharmaceutical tablet wherein the active ingredients are released at a controlled rate selectively in the first portion of the gastrointestinal tract, said tablet having a multi-layer structure and comprising:

a) a first layer, which considerably and rapidly swells in the presence of biological aqueous fluids, said swelling resulting in an increase by at least 50% of the total volume of the tablet when coming into contact with the gastric juice, said layer being formed by a compressed granular mixture of biocompatible hydrophilic polymers and at least one highly swellable (superdisintegrating) polymer selected from the group consisting of cross-linked polyvinylpyrrolidone, hydroxypropylcellulose and hydroxypropyl methylcellulose having molecular weight up to 150,000, cross-linked sodium carboxymethylcellulose, carboxymethyl starch, sodium carboxymethyl starch, potassium methacrylate-divinylbenzene copolymer, polyvinyl alcohols, amylose, cross-linked amylose, starch derivatives, microcrystalline cellulose and cellulose derivatives, alpha-, beta-and gamma-cyclodextrin and dextrin derivatives in general, said substances amounting to 1% to 90% of the layer weight b) a second layer, adjacent to the first and containing the active ingredient, made out of biodegradable and biocompatible polymeric materials and other adjuvants whereby the formulation can be formed by compression and the active ingredient may be released within a time interval that may be predetermined by preliminary tests in vitro;

c) an optional third layer, formed by compression and applied to the second layer, comsprising erodible and/ or gellable and/or swellable hydrophilic polymers and, being initially impermeable to the active ingredient, acting as a barrier modulating the release of the active ingredient contained in the adjacent 2nd layer, said third layer optionally being identical with the first layer in composition and functional characteristics.

2. The pharmaceutical tablet as claimed in claim 1, wherein the first layer besides increasing rapidly in volume exhibits bioadhesion properties whereby the pharmaceutical tablet is maintained in contact with the epithelium of the first portion of the gastroduodenal tract for a long time.

3. The pharmaceutical tablet as claimed in claim 1, wherein the active ingredients may be contained not only in said first layer, but also in said second layer and or/said third layer so that said active ingredients may be released at different times.

4. The pharmaceutical tablet as claimed in claim 1, wherein the active ingredients exhibit a small absorption window in the gastrointestinal tract, i.e. are more effectively absorbed in the stomach, duodenum and in the first portion of the small intestine.

5. The pharmaceutical tablet as claimed in claim 1, wherein the active ingredients contained in the system exert their action mostly at the gastroduodenal level and in the first portion of the small intestine.

6. The pharmaceutical tablet as claimed in claim 1, wherein the active ingredients are selected from the group consisting of prazosin, ketanserin, guanabenz acetate, captopril, captopril hydrochloride, enalapril, enalapril maleate, lysinopril, hydralazide, methyldopa, methyldopa hydrochloride, levodopa, carbidopa, benserazide, amlodipine, nitrendipine, nifedipine, nicardipine, verapamil, acyclovir, inosine, pranobex, tribavirine, vidarabine, zidovudine or AZT.

7. The pharmaceutical tablet as claimed in claim 1, wherein the active ingredients contained in the systems are those exerting a medicinal action at the gastric level, selected from the group consisting of aluminum hydroxide, magnesium carbonate, magnesium oxide, sucralphate, sodium carbenoxolone, pirenzepin, loperamide, cimetidine, ranitidine, famotidine, misoprostol, omeprazol.

8. The pharmaceutical tablet as claimed in claim 1, wherein the polymeric substances used to prepare the 2nd layer, which contains the active ingredient, are hydrophilic and soluble and/or gellable and/or erodible and/or swellable at a different rate in aqueous fluids, and are selected from the group consisting of hydroxymethylcellulose, hydroxyethylcellulose, hydroxypropyl methylcellulose having molecular weight of from 1,000 to 4,000,000, hydroxypropyl cellulose having molecular weight of from 2,000 to 2,000,000, carboxyvinyl polymers, chitosans, mannans, galactomannans, xanthan gums, carrageenin and carrageenans, amylose, alginic acid, salts and derivatives thereof, pectins, acrylates, methacrylates, acrylic/methacrylic copolymers, polyanhydrides, polyamino acids, methyl vinyl ethers/maleic anhydride copolymers, polyvinyl alcohols, glucans, scleroglucans, carboxymethylcellulose and derivatives thereof, ethylcellulose, methylcellulose and polyvinylpyrrolidone.

9. The pharmaceutical tablet as claimed in claim 8, wherein said polymeric substances amount to 5% to 90% by wt. of the layer containing the active ingredient to 85%.

10. The pharmaceutical compressed tablet as claimed in claim 1, wherein a rapid swelling of the swellable layer is favoured by the use of adjuvants classifiable as anionic, cationic and non-ionic surfactants, selected from the group consisting of sodium lauryl sulphate, sodium ricinoleate, sodium tetradecyl sulphate, dioctyl sulphosuccinate, cetomacrogol, poloxamer, glyceryl monostearate, polysorbates, sorbitan monolaurate, lecithins.

11. The pharmaceutical tablet as claimed in claim 1, wherein a rapid swelling of the swellable layer is favoured by the use of adjuvants, classified as effervescent mixtures selected from the group consisting of carbonates and bicarbonates of sodium and of other alkali or alkaline-earth metals, glycocoll sodium carbonate and other salts, either alone or in combination with pharmaceutically acceptable acids, such as citric, tartaric, adipic, ascorbic acids, capable of causing effervescence in an aqueous medium.

12. The pharmaceutical tablet as claimed in claim 1, wherein the thickness of the layers of said tablet may range from 0.2 mm to 8 mm.

13. The pharmaceutical tablet as claimed in claim 1, wherein the layer containing the active ingredient and the barrier layers further contain diluents, binding agents, gliding agents, disgregating agents, colouring agents, lubricants currently used in the pharmaceutical field.

14. The pharmaceutical compressed tablet as claimed in claim 1, wherein water and/or aqueous fluids penetration into the various layers is favoured by including in the formulation hydrophilic diluents, selected from the group consisting of mannitol, lactose, starch of various origin, sorbitol, xylitol, microcrystalline cellulose, colloidal silica.

15. The pharmaceutical tablet as claimed in claim 1, wherein hydrophobic diluents, such as glyceryl monostearate, glyceryl behenate, hydrogenated castor oil, waxes and mono-, bi-, and trisubstituted glycerides, are used when water and/or aqueous fluids penetration into the medicated or barrier layers has to be slowed down.

16. The pharmaceutical tablet as claimed in claim 1, wherein the adjuvants used for the preparation of said barrier layers are selected from the group consisting of glyceryl monostearate and derivative thereof, semisynthetic triglycerides, semisynthetic glycerides, hydrogenated castor oil, glycerylpalmitostearate, glyceryl behenate, cetyl alcohol, polyvinylpyrrolidone, glycerin, ethylcellulose, methylcellulose, sodium carboxymethylcellulose, magnesium stearate, stearic acid, talc, sodium benzoate, boric acid, polyoxyethylene glycols, colloidal silica.

17. The pharmaceutical tablet as claimed in claim 1, wherein the plasticizers used to provide said barrier layers with the elasticity required and to improve their compressibility, adhesion and cohesion, are selected from the group consisting of hydrogenated castor oil, cetyl alcohol, cetylstearyl alcohol, fatty acids, glycerides and triglycerides as are or variously substituted, polyoxyethylene glycols and derivatives thereof having a molecular weight ranging from 400 to 60,000.

* * * * *